(12) United States Patent
Zama et al.

(10) Patent No.: US 7,999,242 B2
(45) Date of Patent: Aug. 16, 2011

(54) SUBSTRATE HOLDING APPARATUS, AND INSPECTION OR PROCESSING APPARATUS

(75) Inventors: Kazuhiro Zama, Mito (JP); Koichi Asami, Kodama (JP); Yusuke Miyazaki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/754,927

(22) Filed: Apr. 6, 2010

(65) Prior Publication Data
US 2010/0196127 A1 Aug. 5, 2010

Related U.S. Application Data

(63) Continuation of application No. 11/896,291, filed on Aug. 30, 2007, now Pat. No. 7,723,709.

(30) Foreign Application Priority Data

Aug. 30, 2006 (JP) ................................. 2006-234631

(51) Int. Cl.
*H01L 21/68* (2006.01)
(52) U.S. Cl. ................. 250/559.14; 414/331.02; 257/48
(58) Field of Classification Search ............. 250/559.14; 414/331.02; 257/48
See application file for complete search history.

(56) References Cited

U.S. PATENT DOCUMENTS

| 5,951,770 | A | 9/1999 | Perlov et al. |
| 6,677,166 | B2 | 1/2004 | Hunter |
| 6,761,362 | B2 | 7/2004 | Noguchi |
| 7,226,055 | B1 * | 6/2007 | Bettencourt et al. ......... 279/106 |
| 7,284,760 | B2 * | 10/2007 | Siebert et al. ................ 279/4.12 |
| 7,703,823 | B2 * | 4/2010 | Harless et al. ............. 294/103.1 |

FOREIGN PATENT DOCUMENTS

| JP | 62-166517 | 7/1987 |
| JP | 2002-319613 | 10/2002 |
| JP | 2004-253756 | 9/2004 |
| JP | 2005-203726 | 7/2005 |
| JP | 2006-210400 | 8/2006 |

OTHER PUBLICATIONS

Japanese Office Action, with English translation, issued in Japanese Patent Application No. 2006-234631, mailed Jul. 13, 2010.

* cited by examiner

*Primary Examiner* — Seung C Sohn
(74) *Attorney, Agent, or Firm* — McDermott Will & Emery LLP

(57) ABSTRACT

In order to enable high accuracy positioning and strong pressing of a substrate, the present invention provides a substrate holding apparatus including: a rotating bed having an inclined surface supporting a lower side of an outer circumferential side surface of the substrate, which bed rotates on a normal line of the substrate as the rotation axis together with the substrate; a position restriction unit rotating together with the rotating bed and restricting the substrate in a predetermined position on the rotating bed by pressing a plurality of points on the circumference on an upper side of the outer circumferential side surface of the substrate prior to the rotation; and a pressing unit rotating together with the rotating bed and pressing the substrate against the inclined surface by pressing a plurality of points on the upper side of the outer circumferential side surface of the substrate during the rotation.

14 Claims, 6 Drawing Sheets

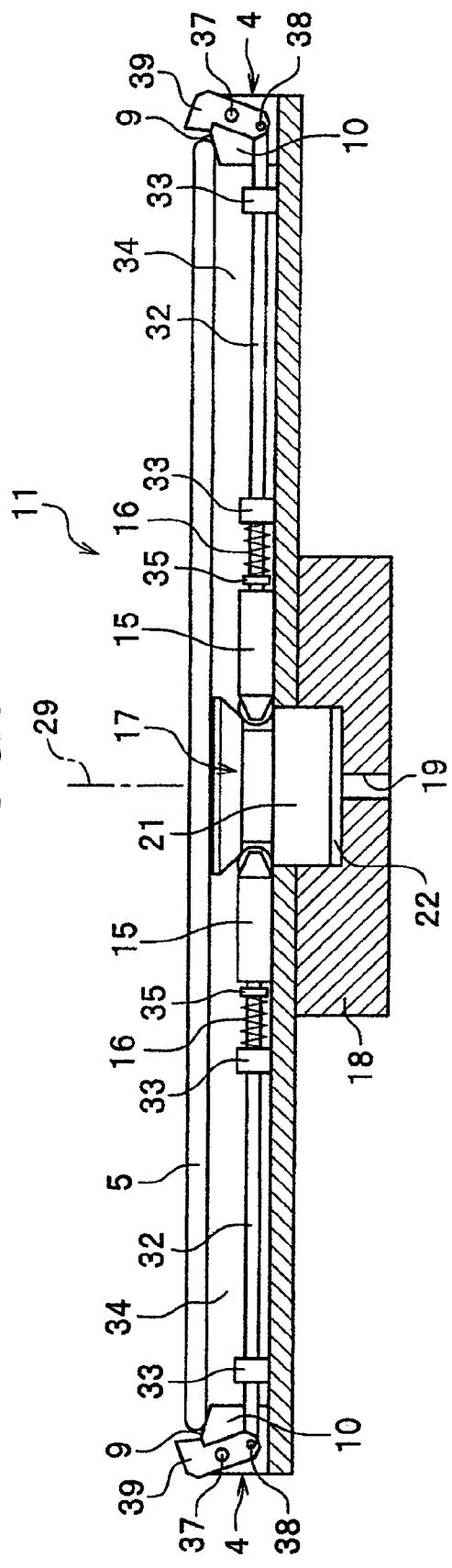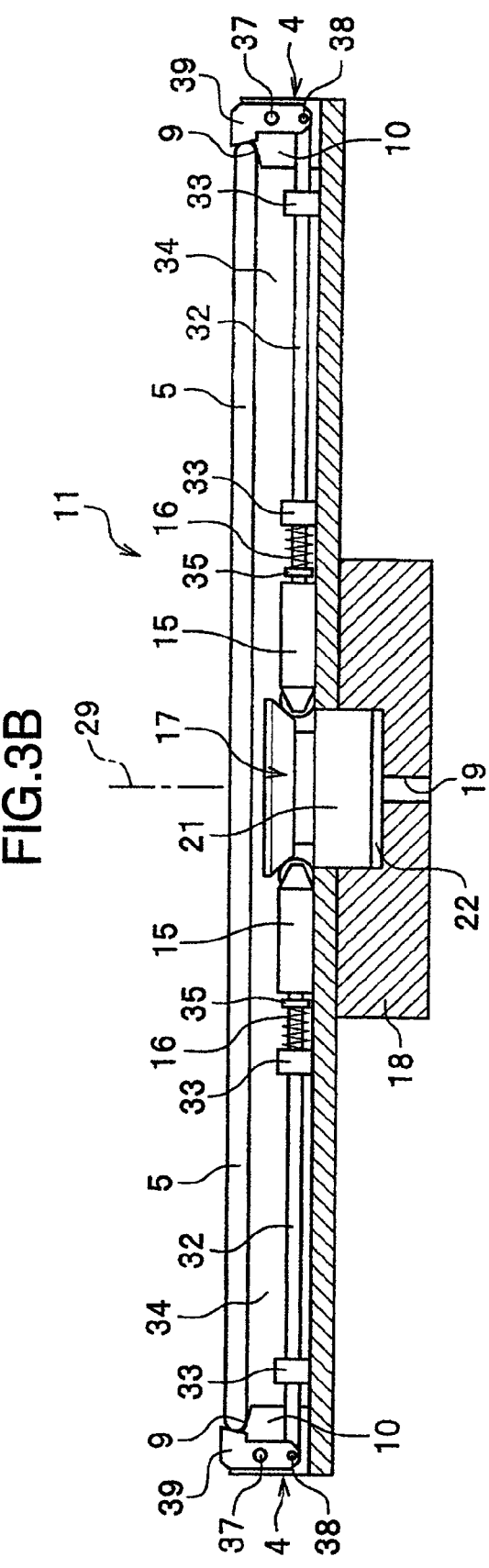

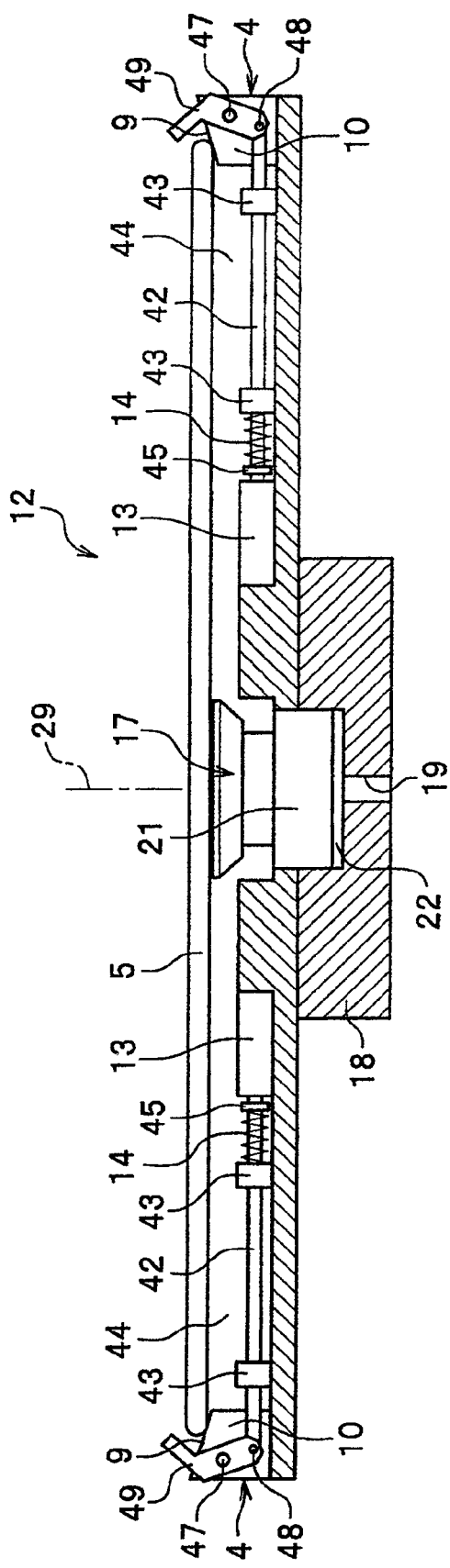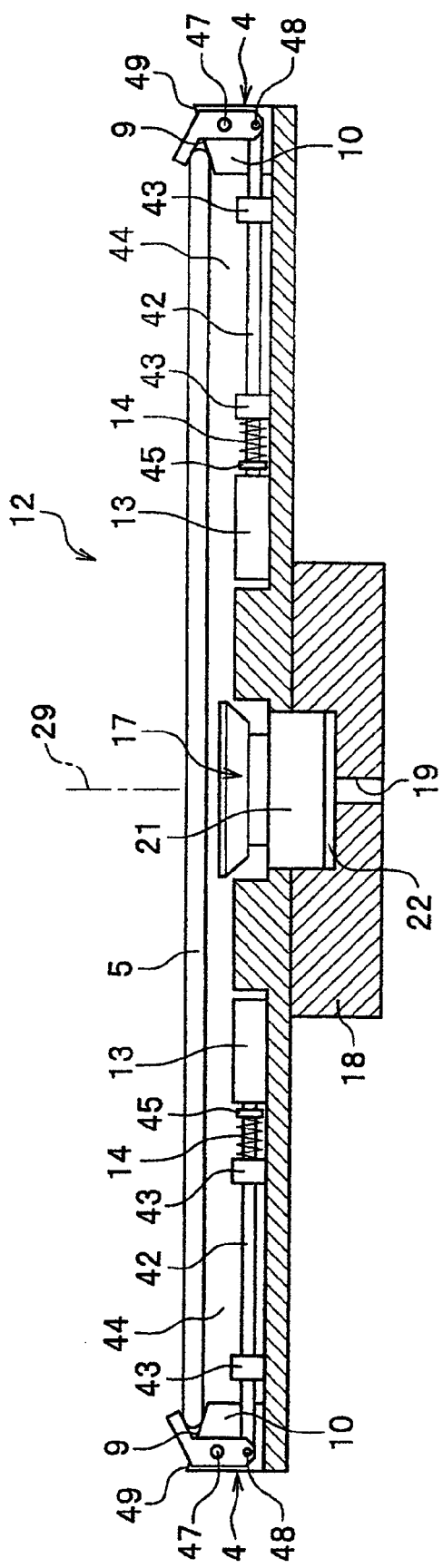

SUBSTRATE HOLDING APPARATUS, AND INSPECTION OR PROCESSING APPARATUS

RELATED APPLICATIONS

This application is a Continuation of U.S. patent application Ser. No. 11/896,291, filed Aug. 30, 2007 now U.S. Pat. No. 7,723,709, claiming priority of Japanese Patent Application No. 2006-234631, filed on Aug. 30, 2006, the entire contents of each of which are hereby incorporated by reference.

BACKGROUND OF THE INVENTION

1. Field of the Invention

The present invention relates to a substrate holding apparatus which rotates together with a substrate while supporting an outer circumferential side surface of the substrate, and an inspection or processing apparatus of a substrate using this substrate holding apparatus.

2. Description of Related Art

In a manufacturing process of a product such as a semiconductor device, a thin display and a magnetic disk, a substrate such as a semiconductor wafer, a glass substrate and a disk substrate is processed, and the processed substrate is inspected. In many cases, the processing and the inspection of the substrate are performed while rotating the substrate. For example, in surface inspection for determining whether a defect such as a flaw or a foreign material is present on a surface of the semiconductor wafer or not, the inspection light scans the surface of the semiconductor wafer in a spiral manner by moving an irradiation region of the inspection light in a radial direction while rotating the semiconductor wafer, to detect the defect or the foreign material on the entire surface of the semiconductor wafer in a short time.

Moreover, in the case of the product such as a semiconductor device, a thin display and a magnetic disk, there is a tendency to control and reduce a defect and a foreign material generated also on a backside of the substrate with miniaturization of a circuit pattern, etc. For this reason, in the manufacturing process thereof, it is necessary to process and inspect the substrate in a non-contact state, not only on the front surface but also on the backside of the substrate.

Accordingly, a substrate holding apparatus which rotates the substrate in a non-contacting state with respect to the front surface and the backside thereof has been proposed (for example, see Paragraphs 0024-0039 and FIGS. 1-4 of JP-A-2004-253756).

BRIEF SUMMARY OF THE INVENTION

In a conventional substrate holding apparatus, in order to make the rotation of a substrate smooth, the substrate is positioned on the substrate holding apparatus so that a normal line of the substrate passing through the center of gravity of the substrate coincides with the rotation axis of the substrate holding apparatus. Then, there is a tendency for a circuit pattern, etc. to be miniaturized, and in order to maintain the repeatability of processing and inspection, it has been considered that it is necessary to improve the positioning accuracy. For example, in the case of a miniaturized circuit pattern, in order to determine on which pattern a foreign material is positioned, it is necessary to improve the accuracy of the coordinate of the foreign material.

In addition, the conventional substrate holding apparatus is not in contact with the backside of the substrate, but alternatively is in contact with a lower side of the rounded outer circumferential side surface of the substrate to support the substrate. The substrate is in contact with an inclined surface of the substrate holding apparatus, which surface is depressed toward the rotation center. Therefore, the substrate is in a horizontal position only when the normal line of the substrate passing through the center of gravity of the substrate coincides with the rotation axis of the substrate holding apparatus, and if those do not coincide with each other even slightly, the substrate will tilt. When an optical device is used for the inspection, the distance between the substrate and the optical device will vary during one revolution. The width of the variation becomes larger than the depth of focus of the optical device, which depth has been reduced corresponding to miniaturization of a pattern, and, it has been considered that this degrades the sensitivity of the optical device.

In addition, the substrate may be warped in the manufacturing process, due to a heating process, or formation of a metal film. In the conventional substrate holding apparatus, the substrate is held while being warped, since the substrate holding apparatus is not in contact with the front surface and the backside of the substrate. Since this warping also causes variation of the distance between the substrate and the optical device, the flatness of the substrate has been improved by blowing a gas with a high cleanliness factor to the backside of the substrate in order to correct the warping. In the future, if the heat processing becomes used frequently or a large number of metal films become formed in a manufacturing process, it is considered that the warping becomes larger, and the blowing for correcting it will become also strong. In order to prevent the substrate from floating up by the blowing, it is considered that stronger force is necessary to press the substrate against the inclined surface which supports the substrate.

In view of the above, the objects of the present invention is to provide a substrate holding apparatus enabling highly accurate positioning and strong pressing of the substrate to solve the above mentioned problems, and to provide an inspection or processing apparatus using this substrate holding apparatus.

In order to solve the above problems, the substrate holding apparatus according to the present invention is characterized by including: a rotating bed; a position restriction unit which rotates together with the rotating bed and restricts the substrate in a predetermined position on the rotating bed by pressing a plurality of points on the circumference on an upper side of an outer circumferential side surface on the substrate prior to the rotation; and a pressing unit which rotates together with the rotating bed and presses the substrate against the inclined surface by pressing a plurality of points on the circumference on the upper side during the rotation. In addition, the inspection or processing apparatus is characterized by performing the inspection or the processing of the substrate using such a substrate holding apparatus while rotating the substrate.

According to the present invention, it is possible to provide a substrate holding apparatus enabling high accuracy positioning and strong pressing of a substrate, and further, provide an inspection or processing apparatus using this substrate holding apparatus.

Other objects, features and advantages of the invention will become apparent from the following description of the embodiments of the invention taken in conjunction with the accompanying drawings.

BRIEF DESCRIPTION OF THE SEVERAL VIEWS OF THE DRAWINGS

FIG. 3A is a cross-sectional view in the A-A direction of FIG. 2 in an un-restricting state;

FIG. 3B is a cross-sectional view in the A-A direction of FIG. 2 in a restricting state;

FIG. 5A is a cross-sectional view in the B-B direction of FIG. 2 in an un-pressing state;

FIG. 5B is a cross-sectional view in the B-B direction of FIG. 2 in a pressing state;

DETAILED DESCRIPTION OF THE INVENTION

Figure 1:
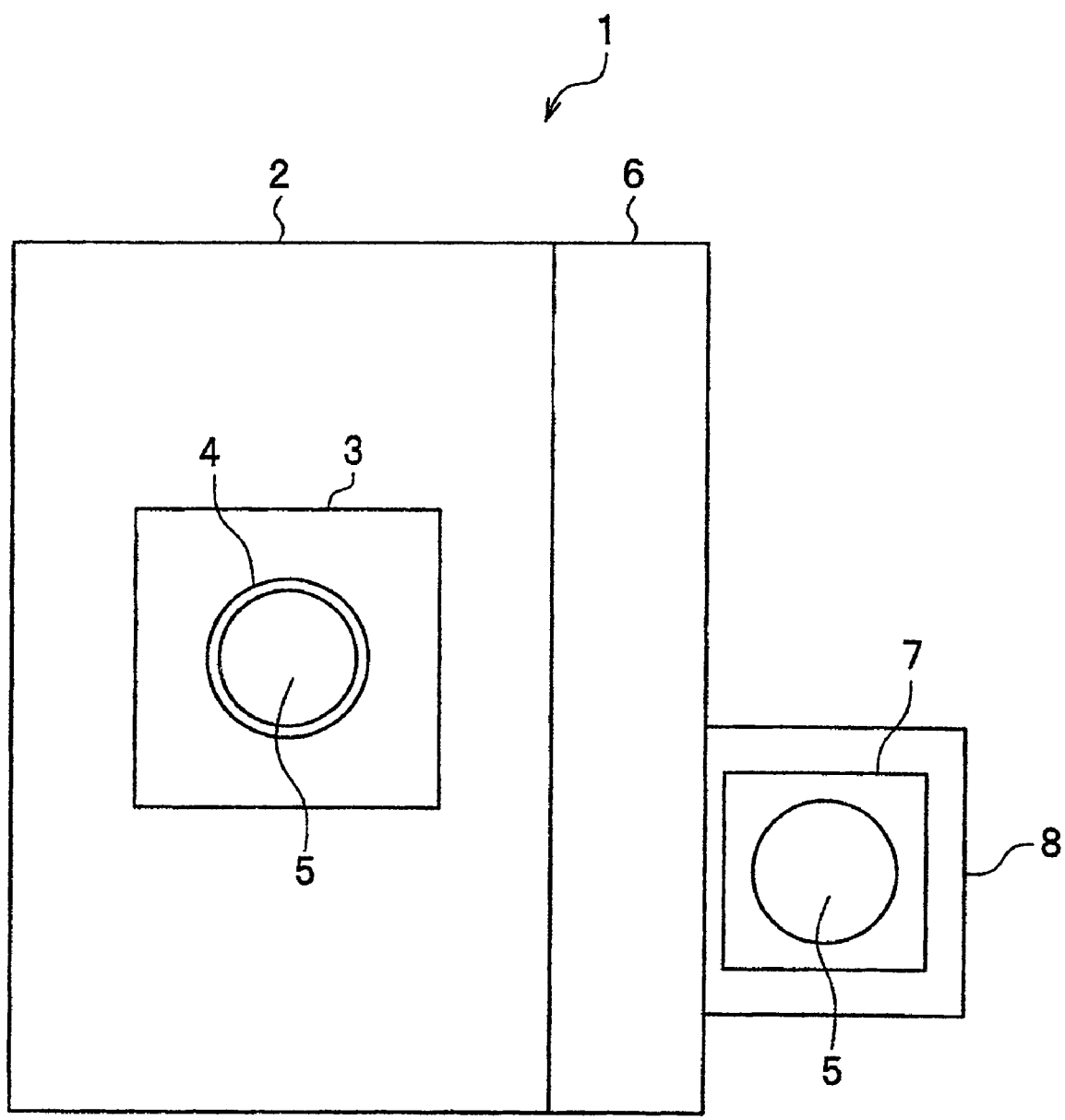
FIG. 1 is a configuration view of an inspection apparatus according to an embodiment.

Next, an embodiment of the present invention will be described in detail with reference to the drawings appropriately. In addition, a common part is denoted by the same reference numeral in the respective drawings, to eliminate duplicate explanation.

An inspection or processing apparatus according to an embodiment of the present invention inspects or processes a substrate such as a semiconductor wafer, a glass substrate and a disk substrate, in a manufacturing process of a product such as a semiconductor device, a thin display and a magnetic disk. As an inspection apparatus, it is used for a surface inspection apparatus which inspects the substrate for defects or foreign materials thereon while rotating the substrate, a particle counter or the like. As a processing apparatus, it is used for a liquid chemical processing apparatus for subjecting the substrate to liquid chemical processing, cleaning and drying while rotating the substrate, a spin coater for coating, developing and releasing of a resist or the like. In the following descriptions, a semiconductor wafer is mainly supposed as a substrate, and a surface inspection apparatus is mainly supposed as an inspection or processing apparatus.

As illustrated in FIG. 1, the inspection apparatus (surface inspection apparatus) 1 according to the embodiment of the present invention is composed of an inspection section 2 for directly inspecting a substrate (a semiconductor wafer) 5, a substrate transferring robot 6, and a cassette table 8. To the cassette table 8, a cassette 7 storing a plurality of substrates 5 therein is transferred. In the cassette 7, the plurality of substrates 5 are stored at even intervals in the depth direction of the drawing. When replacing the inspection apparatus 1 by a processing apparatus, the inspection section 2 may be replaced by a processing section for directly performing processing.

The inspection section 2 is provided with a substrate holding apparatus 3. The substrate holding apparatus 3 is provided with a rotatable rotating bed 4. The substrate transferring robot 6 transfers the substrate 5 from the cassette 7 onto the rotating bed 4, and transfers the substrate 5 from the rotating bed 4 onto the cassette 7.

A light-projecting system and a light-receiving system (which are not shown in the drawing) are disposed above the rotating bed 4. The light-projecting system radiates a light beam such as a laser light on a surface of the substrate 5 mounted on the rotating bed 4. By linearly transferring the substrate holding apparatus 3 in a radial direction of the substrate 5 while rotating the substrate 5 by the rotating bed 4, the light beam radiated from the light-projecting system scans the surface of the substrate 5 in a spiral manner. The light-receiving system detects a reflected light or a scattered light from the surface of the substrate 5. A detected signal from the light-receiving system is processed by an image signal processing device (not shown) so that a foreign material existing on the surface of the substrate 5 is detected.

Figure 2:
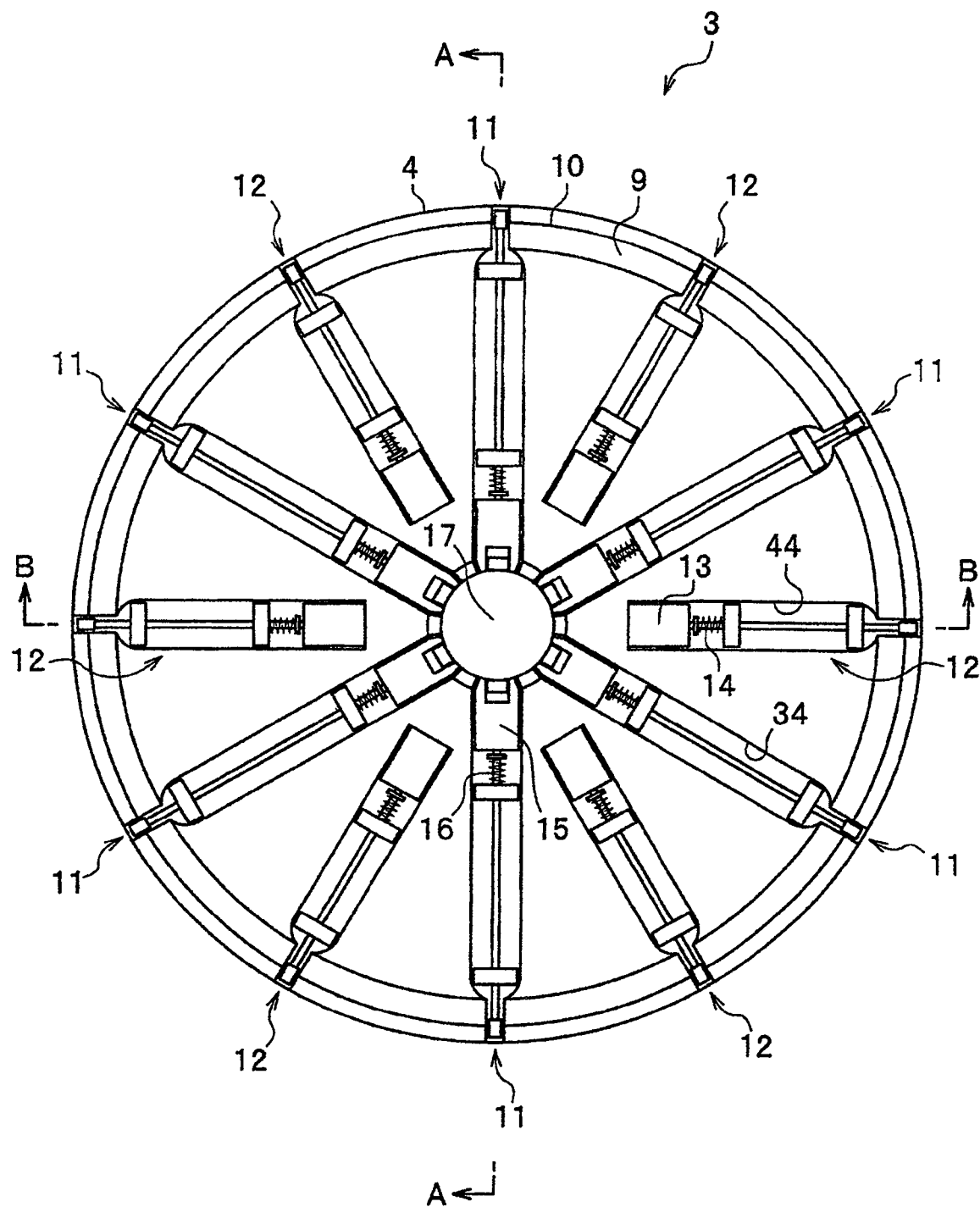
FIG. 2 is a plane view of a substrate holding apparatus according to the embodiment.

As shown in FIG. 2, the substrate holding apparatus 3 includes: a rotating bed 4 which rotates together with the substrate 5; position restriction units 11 which rotate together with the rotating bed 4, and are arranged so as to extend radially in six directions at even intervals and at even angles, from the center of the rotating bed 4 to an outer circumference thereof; and six pressing units which rotate together with the rotating bed 4, and are arranged radially at even intervals and at even angles in a region of the rotating bed 4 between the position restriction units 11, which region the outer circumference of the rotating bed 4.

The outer circumference of the rotating bed 4 is provided with a tilting bed 10 having an inclined surface 9 for supporting a lower side of a rounded outer circumferential side surface of the substrate 5. In the rotating bed 4, grooves 34 and grooves 44 are formed radially, so that the position restriction units 11 are formed in the grooves 34 and the pressing units 12 are formed in the grooves 44.

The position restriction unit 11 can hold the substrate 5 in a predetermined position on the rotating bed 4 prior to rotation. As a predetermined position, a position where a normal line of the substrate 5 passing through the center of gravity of the substrate 5 coincides with the rotation axis of the substrate holding apparatus 3 is set in order to smoothly rotate the substrate 5. In addition, when the position of the center of gravity of the substrate 5 is hardly determined due to an orientation flat thereof, the center of the substrate 5 may be used instead of the center of gravity thereof. In this manner, by retaining the substrate 5 at a predetermined position on the rotating bed 4, the substrate can be positioned on the substrate holding apparatus. The pressing unit 12 presses the substrate 5 against the inclined surface 9 during rotation. In this manner, the position restriction unit 11 is specialized in positioning, and the pressing unit is specialized in pressing. In addition, the center of the position restriction unit 11 is provided with a displacing unit 17. The displacing unit 17 is displaced by operation from the outside of the substrate holding apparatus 3, and the position restriction units 11 perform positioning by utilizing this displacement as driving force.

Hereinafter, the position restriction unit 11 and the pressing unit 12 will be described in detail. First, the position restriction unit 11 will be described.

As shown in FIG. 3A, the rotating bed 4 is attached to a spindle 18, and rotated around a rotation axis 29 by rotation of a motor (not shown) connected to the spindle 18. The inclined surface 9 of the tilting bed 10 is adapted to come down as the inclined surface 9 approaches to the rotation center through which the rotation axis 29 passes. The spindle 18 is provided with an air passage 19. Using an air pump (not shown), compressed air is supplied or exhausted through the air passage 19.

Figure 4A:
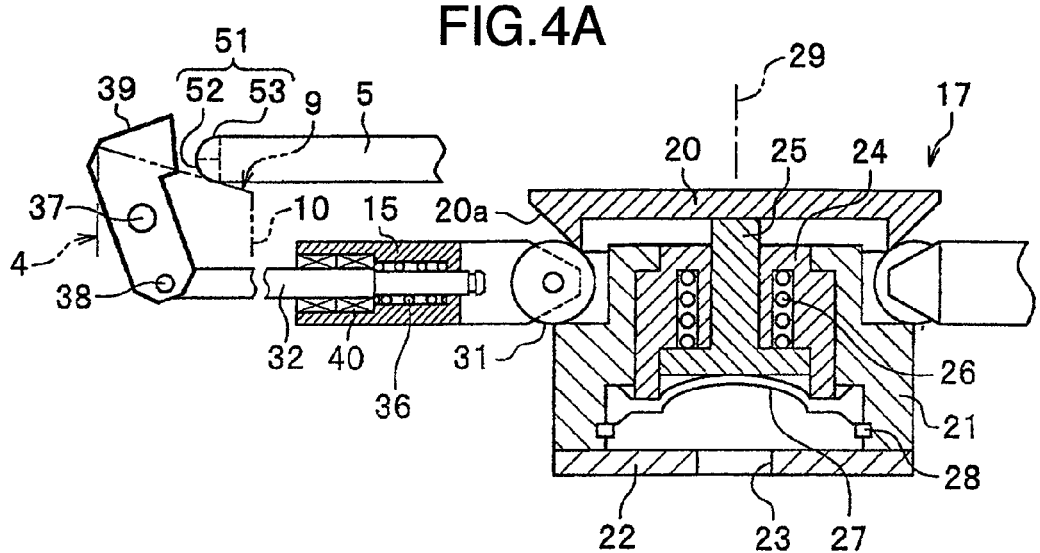
FIG. 4A is a cross-sectional view of a position restriction unit of the substrate holding apparatus in an un-restricting state.

As shown in FIGS. 3A and 4A, in each groove 34, a claw 39 is attached to the vicinity of the outer circumference of the rotating bed 4 by a pin 37 which works as a fulcrum. One end of the shaft 32 is connected to the power point of the claw 39 by a pin 38, in each groove 34. The shaft 32 is arranged radially from the rotation center passing through the rotation axis 29. A restriction movable piece 15 is connected to the other end of the shaft 32.

The shaft 32 is slidably supported by shaft receivers 33 fixed to the rotating bed 4, and biased toward the rotation center of the rotation axis 29 of the rotating bed 4 by a restriction elastic body 16 inserted between a retaining ring 35 fixed to the shaft 32 and one of the shaft receiver 33. A spring can be used as the restriction elastic body 16, however, it may be also possible to use not only elastic force of the spring, but also elastic force of rubber, or repulsive force of a magnet as long as such biasing is achieved.

A perforated hole is formed in the restriction movable piece 15, and the shaft 32 is inserted in the perforated hole. The diameter of the tip of the shaft 32 is made smaller than those of the other portions of the shaft, and a spring 36 is inserted so as to be caught by a step formed thereby. The shaft 32 is slidably supported by a slider 40 fixed to the restriction movable piece 15. If the restriction movable piece 15 is displaced into the horizontal direction toward the claw 39, the spring 36 is compressed so that the shaft 32 can be biased to be pushed toward the claw 39 in a horizontal direction with the biasing force in proportion to the compression amount.

As shown in FIG. 4A, the restriction movable piece 15 is provided with a roller 31 on an opposite side to the shaft 32. The roller 31 rolls on a tapered plane 20a of an elevating plate 20 which is displaced in an up-and-down direction by the displacing unit 17, in synchronization with the displacement of the elevating plate 20. This causes the up-and-down displacement of the elevating plate 20 to be converted into the horizontal displacement of the restriction movable piece 15.

The displacing unit 17 includes: a cover 22 having an air port 23 communicating with the air passage 19 in FIG. 3A; a case 21 covering the interior along with the cover 22; a diaphragm 27 moving up-and-down by the pressure of compressed air; a retaining ring 28 stopping the diaphragm 27; a stopper 25 moving up-and-down together with the diaphragm 27; a bushing 24 supporting the stopper 25 so as to be slidable in the up-and-down direction; a spring 26 which is compressed as the stopper 25 ascends and biases the stopper 25 so as to descend, so that the diaphragm 27 and the stopper 25 are interlocked; and the elevating plate 20 fixed to the stopper 25.

The outer circumference of the substrate 5 is chamfered so that the outer circumferential side surface 51 of the substrate 5 is rounded, protruded, and swollen. The inclined surface 9 of the tilting bed 10 supports the lower side 52 of the outer circumferential side surface 51 of the substrate 5.

FIGS. 3A and 4A show a state where the substrate 5 is not restricted in the predetermined position by the claw 39 of the position restriction unit 11. The compressed air is supplied into the air channel 19, and the diaphragm 27 is pressed by the compressed air so as to be convex upwardly, so that the central part of the diaphragm 27 is ascended. In accordance with this ascent, the stopper 25 and the elevating plate 20 are ascended. By the biasing force of the restriction elastic body 16, the roller 31 rolls into a space formed after the elevating plate 20 is ascended, and the restriction movable piece 15 moves toward the rotation center of the rotation axis 29 of the rotating bed 4. The shaft 32 also moves toward the rotation center. The lower portion of the claw 39 is moved toward the rotation center, and the upper portion of the claw 39 is moved backward from the rotation center. Since the upper portion of the claw 39 is moved backward from the rotation center, the claw 39 becomes in a so-called open state, resulting in an un-restricted state of the substrate 5. In the un-restricted state, it is possible to mount the substrate 5 on the rotating bed 4 and to take out the substrate 5 from the rotating bed 4 by the substrate transferring robot 6, while stopping rotation of the rotating bed 4.

Figure 4B:
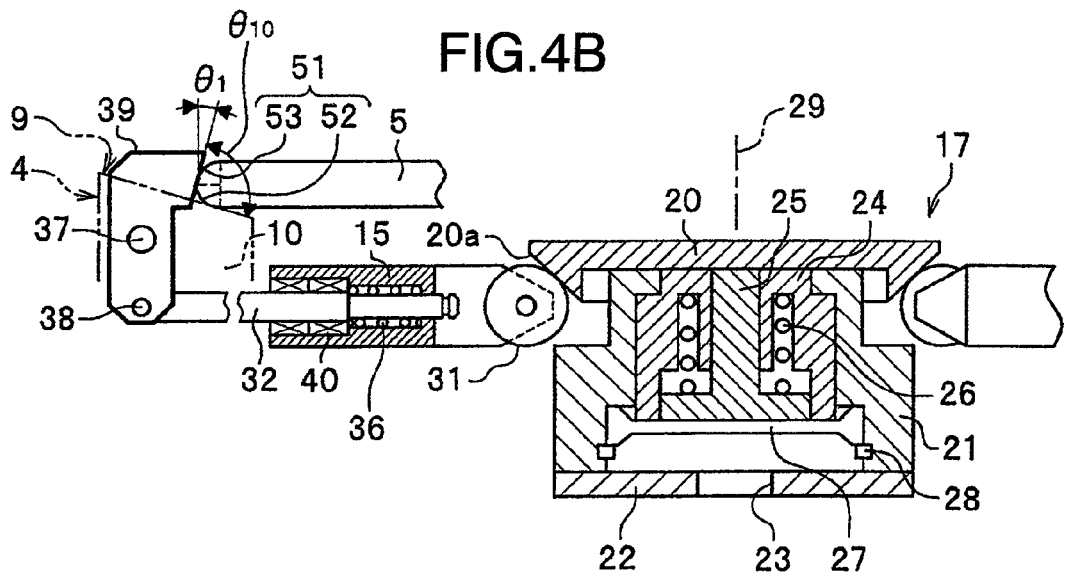
FIG. 4B is a cross-sectional view of the position restriction unit of the substrate holding apparatus in a restricting state.

FIGS. 3B and 4B show a state where the substrate 5 is restricted by the claw 39 of the position restriction unit 11 in the predetermined position. The compressed air is exhausted through the air passage 19, and therefore the diaphragm 27 becomes flat. The stopper 25 and the elevating plate 20 are descended by the biasing force of the spring 26, so that the elevating plate 20 is brought into contact with the case 21. The roller 31 rolls out from the space closed by descent of the elevating plate 20, and the restriction movable piece 15 is moved in a direction away from the rotation center of the rotation axis 29 of the rotating bed 4. The shaft 32 is also moved in the direction away from the rotation center. The lower portion of the claw 39 is moved in the direction away from the rotation center, and the upper portion of the claw 39 is moved in a direction toward the rotation center. By the fact that the upper portion of the claw 39 is moved in the direction toward the rotation center, the claw 39 becomes in a so-called closed state, and pushes a plurality of positions on the circumference of the upper side 53 of the outer circumferential side surface 51 prior to the rotation. The contact point of the claws 39 contacting with the upper side 53 of the outer circumferential side surface 51 is a so-called point of action, and set on a lower side of a region of the upper side 53 of the outer circumferential side surface 51. That is, the angle $\theta 1$ formed by a contact surface of the claw 39 pressing the upper side 53 of the outer circumferential side surface 51 and the rotation axis 29, which angle is equal to or smaller than 90°, is set to be equal to or smaller than 60° and preferably set to be equal to or smaller than 30°. Moreover, the angle $\theta 10$ formed by the contact surface of the claw 39 and the inclined surface 9 of the tilting bed 10 is set to be equal to or greater than 90°.

Since the claw 39 is in contact with and presses the upper side 53 of the outer circumferential side surface 51 of the substrate 5 in this manner, the substrate 5 can be pressed in a direction toward the rotation center, without pressing the substrate 5 strongly against the tilting bed 10 by the claw 39. Since the substrate 5 is not pressed strongly against the tilting bed 10, strong static frictional force and dynamic frictional force do not occur between the substrate 5 and the tilting bed 10, and thus the substrate 5 can be moved more easily and surely just by a pushing amount by pushing the substrate 5 in the direction toward the rotation center. Since the pressing is simultaneously performed in the six directions from the outer circumferential side surface of the rotating bed 4 toward the rotation center as shown in FIG. 2, the substrate 5 can be reliably moved so that the substrate 5 is in the predetermined position, namely, the center of the substrate 5 coincides with the rotation center, which enables high accuracy positioning. As a result, the substrate 5 can be restricted in the predetermined position with high accuracy.

When the substrate 5 is in a restricted state, the substrate 5 can be also rotated together with the rotating bed 4 by rotating the rotating bed 4. Since the substrate 5 is not pressed against the tilting bed 10 with strong force, air blowing from a backside of the substrate 5 for correcting the warping of the substrate 5 has not yet been performed. The substrate holding apparatus 3 can control the un-restricting and restricting of the substrate 5 by supplying and exhausting the compressed air from the outside of the substrate holding apparatus 3.

Figure 4C:
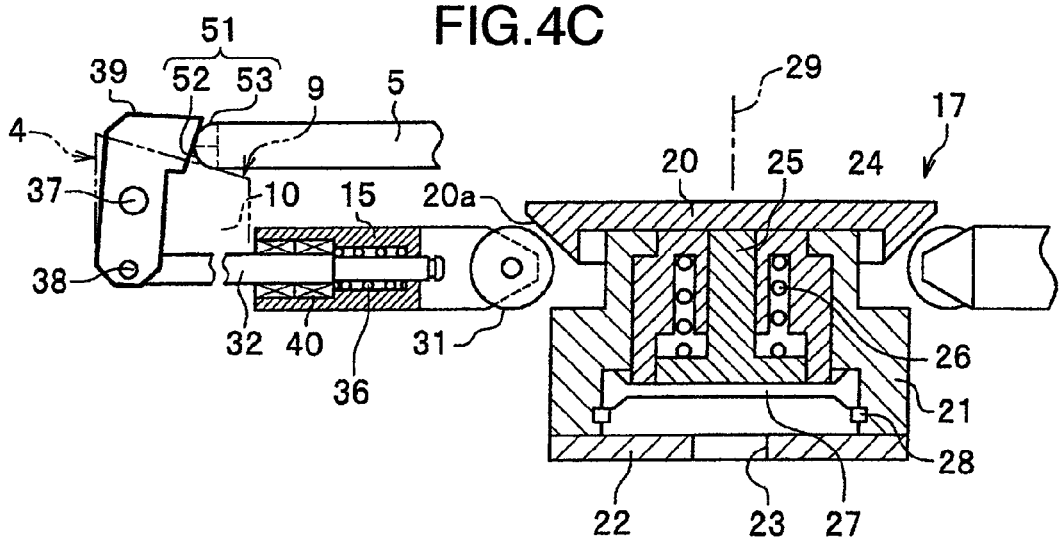
FIG. 4C is a cross-sectional view of the position restriction unit of the substrate holding apparatus in a restricting and high speed rotation state.

FIG. 4C shows a state where the rotating bed 4 and the substrate 5 are rotated at a high speed while the substrate 5 is restricted in the predetermined position by the claws 39 of the position restriction units 11. The high speed rotation causes centrifugal force acting on the restriction movable piece 15 of the position restriction unit 11 rotating together with the rotating bed 4, and the restriction movable piece 15 is moved in the direction toward the claw 39 and away from the elevating plate 20. The shaft 32 is also moved in the direction further away from the rotation center as compared to the case in FIG. 4B. The lower portion of the claw 39 is moved in the direction away from the rotation center, and the upper portion of the claw 39 is moved in a direction further toward the rotation center as compared to the case in FIG. 4B. The movement of the upper portion of the claw 39 toward the rotation center enables the claw 39 to restrict the substrate 5 in the predetermined position by stronger force. Since the restricting force is originated from the centrifugal force, the restricting force becomes larger in proportion to the rotation speed. This means that the substrate 5 can be restricted surely because, even if the center of the substrate 5 is slightly shifted from the rotation center, and the centrifugal force due to high speed rotation acts on the substrate 5, and further, even if the centrifugal force acting on the substrate 5 is increased by increase in rotation speed, the force restricting the substrate 5 in the predetermined position is also increased.

In addition, since the substrate 5 is a rigid body in general, the substrate 5 cannot be visibly compressed in the direction toward the rotation center as shown by the change from FIG. 4B to FIG. 4C. Alternatively, the spring 36 in the restriction movable piece 15 is compressed. By the biasing force of the compressed spring 36, the shaft 32 is pressed in the direction away from the rotation center, the lower portion of the claw 39 is also pressed in the direction away from the rotation center, and finally the upper portion of the claw 39 can press the substrate 5 in the direction toward the rotation center with force which is proportional to the rotation speed.

The above describes the position restriction unit 11 in detail. Hereinafter, the pressing unit 12 will be described.

Figure 6A:
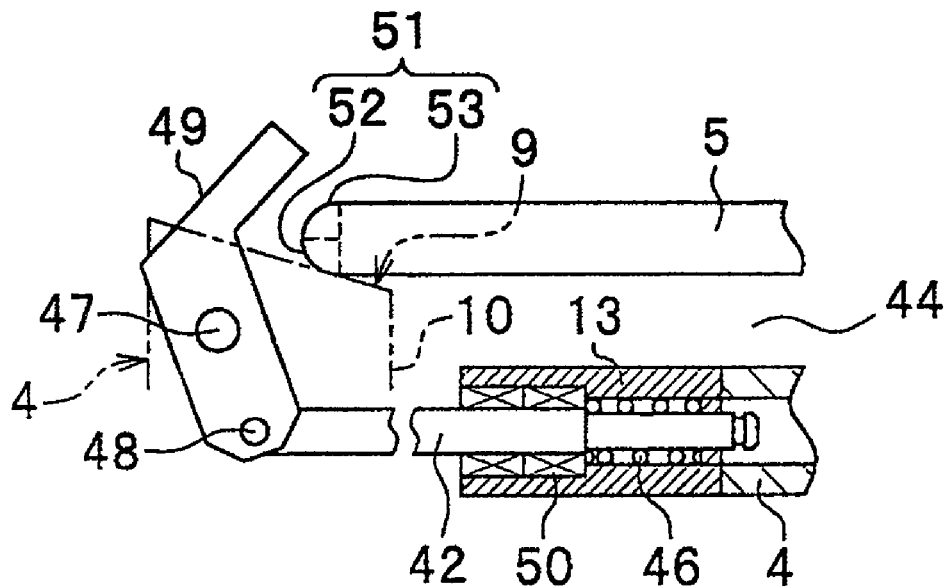
FIG. 6A is a cross-sectional view of a pressing unit of the substrate holding apparatus in an un-pressing state.

As shown in FIGS. 5A and 6A, a claw 49 is attached in the groove 44 by a pin 47 acting as a power point near the outer circumference of the rotating bed 4. The power point of the claw 49 is connected to one end of a shaft 42 by a pin 48. The shaft 42 is arranged radially from the rotation center through which the rotation axis 29 passes. A pressing movable piece 13 is connected to the other end of the shaft 42.

The shaft 42 is slidably supported by shaft receivers 43 fixed to the rotating bed 4 and biased in a direction toward the rotation center of the rotation axis 29 of the rotating bed 4 by a pressing elastic body 14 inserted between a retaining ring 45 fixed to the shaft 42 and the shaft receiver 43. Although a spring may be used as the pressing elastic body 14, it may be possible to utilize not only elastic force of the spring but also elastic force of rubber, or repulsive force of a magnet as long as such biasing can be achieved.

A perforated hole is formed in the pressing movable piece 13, and the shaft 42 is inserted in the perforated hole. The diameter of the tip of the shaft 42 is made smaller than those of the other portions of the shaft, and a spring 46 is inserted so as to be caught by a step formed thereby. The shaft 42 is slidably supported by a slider 50 fixed to the pressing movable piece 13. If the pressing movable piece 13 is displaced into the horizontal direction toward the claw 49, the spring 46 is compressed so that the shaft 42 can be biased to be pushed in the direction toward the claw 49 with the biasing force in proportion to the compression amount.

FIGS. 5A and 6A show a state where the substrate 5 is not pressed against the tilting bed 10 by the claw 49 of the pressing unit 12. In the state, the rotating bed 4 is not rotated, or is rotated at a low speed. The position restriction unit 11 may be in a state where the substrate 5 is not restricted, or in a state where the substrate 5 is restricted.

By the biasing force of the pressing elastic body 14, the pressing movable piece 13 is moved in the direction toward the rotation center of the rotation axis 29 of the rotating bed 4, and pressed against a step of the rotating bed 4. The shaft 42 is also moved in the direction toward the rotation center. The lower portion of the claw 49 is moved in the direction toward the rotation center, and the upper portion of the claw 49 is moved in a direction away from the rotation center. Since the upper portion of the claw 49 is moved in the direction away from the rotation center, the claw 49 becomes in a so called open state, resulting in a state where the substrate 5 is not pressed against the tilting bed 10. In the un-pressed state, if the rotating bed 4 is not rotated, and the position restriction unit 11 is also in an un-restricted state, it is possible to mount the substrate 5 on the rotating bed 4 by the substrate transferring robot 6, and to take out the substrate 5 from the rotating bed 4. Moreover, even in the un-pressed state, it is possible to rotate the rotating bed 4 while causing the position restriction unit 11 to be in the restricted state.

Figure 6B:
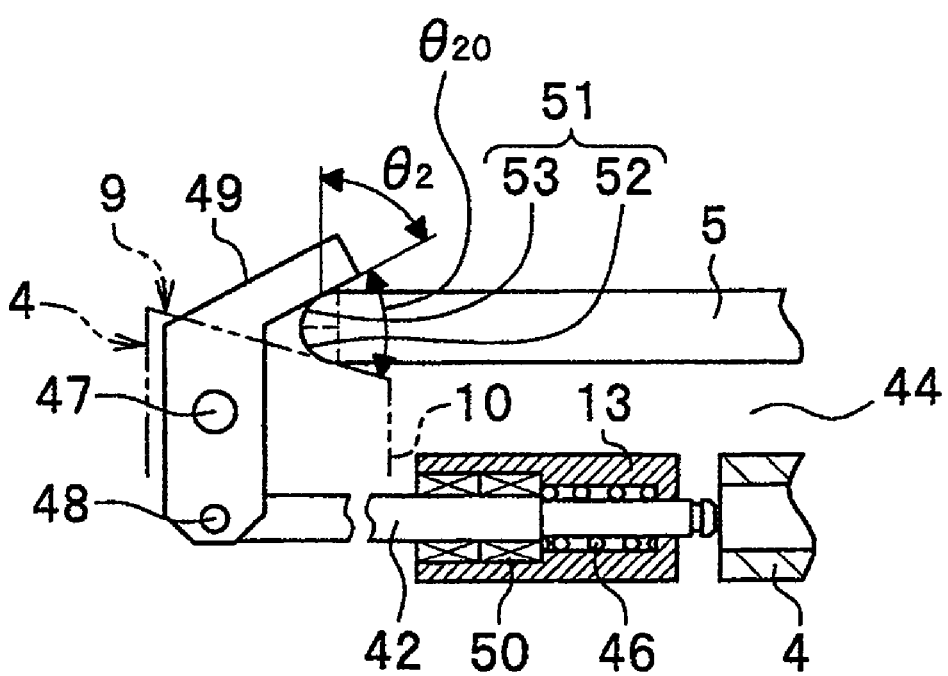
FIG. 6B is a cross-sectional view of the pressing unit of the substrate holding apparatus in a pressing state.

FIGS. 5B and 6B show a state where the substrate 5 is pressed against the tilting bed 10 by the claw 49 of the pressing unit 12. In the pressed state, the rotating bed 4 is rotated together with the substrate 5 at a high rotation speed while the position restriction unit 11 causes the substrate 5 to be in the restricted state. Since the rotating bed 4 is rotated at a high speed, centrifugal force acts on the pressing movable piece 13 of the pressing unit 12, and the pressing movable piece 13 is moved in the direction away from the step of the rotating bed 4 and in the direction toward the claw 49. The shaft 42 is also moved in the direction away from the rotation center. The lower portion of the claw 49 is moved in the direction away from the rotation center, and the upper portion of the claw 49 is moved in the direction toward the rotation center. Since the upper portion of the claws 49 is moved in the direction toward the rotation center, the claw 49 becomes in a so-called closed state, and pushes a plurality of positions on the circumference of the upper side 53 of the outer circumferential side surface 51 of the substrate during the rotation. The contact point of the claws 49 contacting with the upper side 53 of the outer circumferential side surface 51 becomes a point of action, and is set in an upper portion of a region of the upper side 53, which contact point is higher in level than that of the contact point of the claws 39 of the position restriction units 11. In other words, the angle θ2 formed by a contact surface of the claw 49 pressing the upper side 53 of the outer circumferential side surface 51 and the rotation axis 29, which is equal to or smaller than 90°, is greater than 60°. Moreover, the angle θ20 formed by the contact surface of the claw 49 and the inclined surface 9 of the tilting bed 10 is set to be smaller than 90°, and is smaller than the angle θ10 formed by the contact surface of the claw 39 of the position restriction unit 11 and the tilted surface 9 of the tilting bed 10.

Since the claw 49 is in contact with and presses the upper side 53 of the outer circumferential side surface 51 of the substrate 5 in this manner, the substrate 5 can be strongly pressed against the tilting bed 10 by the claw 49. By pressing the substrate 5 strongly against the tilting bed 10, strong static frictional force and dynamic frictional force are caused between the substrate 5 and the tilting bed 10, whereby, even if the substrate 5 is pressed in the direction toward the rotation center, the substrate 5 hardly moves while sliding on the tilting bed 10. In other words, even in the case of high speed rotation, it is possible to maintain high accuracy positioning by the position restriction unit 11. Moreover, since the substrate 5 is strongly pressed against the tilting bed 10, air can be brown on the substrate 5 from the backside thereof in order to correct the warping of the substrate 5. Since this pressing force is originated from the centrifugal force of the rotation, the pressing force can be made larger in proportion to the rotation speed, the weight of the pressing movable piece 13 and the distance of the pressing movable piece 13 from the rotation center, which allows the pressing force to be set in accordance with the strength of air blowing.

Since the pressing unit 12 does not have a mechanism controlled by compressed air from the outside as compared to the case of the position restriction unit 11, the pressing unit 12 can be miniaturized and arranged on the rotating bed 4 in a space formed after arranging the position restriction units 11.

In addition, when the centrifugal force acting on the pressing movable piece 13 becomes larger, the spring 46 inside the movable piece 13 is compressed. By the biasing force of the compressed spring 46, the shaft 42 is pushed in the direction away from the rotation center, the lower portion of the claw 49 is also pressed in the direction away from the rotation center, and finally the upper portion of the claw 49 can press the substrate 5 in the direction toward the rotation center with force which is proportional to the rotation speed.

In this manner, positioning is performed by restricting the substrate 5 using the position restriction unit 11; by rotating the rotating bed 4 together with the substrate 5, the substrate 5 is pressed against the rotating bed 4 using the pressing unit 12 by the centrifugal force of the rotation; the substrate 5 is corrected by blowing air from the backside thereof; and inspection of the substrate 5 is performed at the inspection section 2. When the inspection is completed, the air blowing for correction is stopped, and the rotation is stopped. By stoppage of the rotation, the position restriction unit 11 becomes in the state of FIG. 4B from the state of FIG. 4C, and the pressing unit 12 becomes in the state of FIG. 5A from the state of FIG. 5B. Since the centrifugal force does not act thereon, the pressing elastic body 14 causes the pressing movable piece 13 to move back, and releases the substrate 5 from the pressing. Finally, by supplying compressed air into the displacing unit 17, the position restriction unit 11 becomes in the state of FIG. 3A from the state of FIG. 3B, and the restriction elastic body 16 causes the restriction movable piece 15 to move back and releases the substrate 5 from the restriction in the predetermined position. Accordingly, the substrate 5 can be transferred from the rotating bed 4 to the cassette 7 by the substrate transferring robot 6.

According to the present embodiment, since the substrate holding apparatus 3 is brought into contact only with the outer circumferential side surface of the substrate 5 without being brought into contact with the front surface and the backside of the substrate 5, pollution of the substrate 5 can be reduced. Furthermore, high accuracy positioning and strong pressing of the substrate can be achieved.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection apparatus which inspects a defect of a substrate comprising:
    a holding unit which holds the substrate;
    a light projecting unit which irradiates the substrate with light;
    a light receiving unit which receives a light from the substrate; and
    a processing unit which detects the defect based on a result in response to the received light, wherein said holding unit comprises:
    a rotating unit which rotates the substrate;
    a plurality of position restriction units which restrict the substrate corresponding to rotation of the rotating unit;
    a plurality of pressing units which press the substrate corresponding to rotation of the rotating unit, and
    the position restriction units include first claws, wherein:
    the first claws are formed at sides of an outer periphery of each of the restriction units and contact with and press upper sides of the outer peripheral sides of the substrate, and
    a contact surface of a first claw that presses the upper side of the outer peripheral side of the substrate and a rotation axis of the substrate forms an acute angle.

2. An inspection apparatus according to claim 1, wherein the position restriction units are different from the pressing units.

3. An inspection apparatus according to claim 1, wherein the position restriction units are specialized in positioning.

4. An inspection apparatus according to claim 1, wherein the pressing units are specialized in pressing.

5. An inspection apparatus according to claim 1, wherein the position restriction units are formed in a radial fashion toward the outer periphery of the holding unit from a center of the rotating unit.

6. An inspection apparatus according to claim 1, wherein the pressing units are formed in a radial fashion toward the outer periphery of the holding unit from a center of the rotating unit.

7. An inspection apparatus according to claim 1, wherein:
    the pressing units include second claws, and
    the second claws are formed at the sides of the outer periphery of each of the pressing units and contact with and press the upper sides of the outer peripheral sides of the substrate.

8. A substrate holding apparatus, for an inspection apparatus, comprising:
    a rotating unit which rotates the substrate;
    a plurality of position restriction units which restrict the substrate corresponding to rotation of the rotating unit; and
    a plurality of pressing units which press the substrate corresponding to rotation of the rotating unit, wherein:
    the position restriction units include first claws,
    the first claws are formed at sides of an outer periphery of each of the restriction units and contact with and press the upper sides of the outer peripheral sides of the substrate, and
    a contact surface of a first claw that presses the upper side of the outer peripheral side of the substrate and a rotation axis of the substrate forms an acute angle.

9. An inspection apparatus according to claim 8, wherein the position restriction units are different from the pressing units.

10. An inspection apparatus according to claim 8, wherein the position restriction units are specialized in positioning.

11. An inspection apparatus according to claim 8, wherein the pressing units are specialized in pressing.

12. An inspection apparatus according to claim 8, wherein the position restriction units are formed in a radial fashion toward the outer periphery of the holding unit from a center of the rotating unit.

13. An inspection apparatus according to claim 8, wherein the pressing units are formed in a radial fashion toward the outer periphery of the holding unit from a center of the rotating unit.

14. An inspection apparatus according to claim 8, wherein:
    the pressing units include second claws, and
    the second claws are formed at sides of the outer periphery of each of the pressing units and contact with and press the upper sides of the outer peripheral side of the substrate.

* * * * *